(12) United States Patent
Funt

(10) Patent No.: US 6,276,935 B1
(45) Date of Patent: *Aug. 21, 2001

(54) MEDICAL RESERVOIR SYSTEM

(76) Inventor: Lawrence A. Funt, 5416 Edgemoor La., Bethesda, MD (US) 20814

(*) Notice: Subject to any disclaimer, the term of this patent is extended or adjusted under 35 U.S.C. 154(b) by 0 days.

This patent is subject to a terminal disclaimer.

(21) Appl. No.: 09/486,796
(22) PCT Filed: Sep. 4, 1998
(86) PCT No.: PCT/US98/18596
  § 371 Date: Mar. 2, 2000
  § 102(e) Date: Mar. 2, 2000
(87) PCT Pub. No.: WO99/11194
  PCT Pub. Date: Mar. 11, 1999

Related U.S. Application Data

(63) Continuation-in-part of application No. 08/924,800, filed on Sep. 5, 1997, now Pat. No. 5,842,860.

(51) Int. Cl.$^7$ ..................................................... A61G 17/02
(52) U.S. Cl. .............................. 433/80; 433/215; 433/229
(58) Field of Search ............................. 433/80, 215, 216, 433/229

(56) References Cited

U.S. PATENT DOCUMENTS

| | | | |
|---|---|---|---|
| 1,586,302 | * 5/1926 | Funk | 433/80 |
| 3,503,127 | 3/1970 | Kasdin | 433/229 |
| 3,600,807 | 8/1971 | Sipos | 433/229 |

(List continued on next page.)

FOREIGN PATENT DOCUMENTS

| | | | |
|---|---|---|---|
| 1669445 | 8/1991 | (SU) | 433/215 |

OTHER PUBLICATIONS

The Journal of Prosthetic Dentistry, vol. 52, No. 4, pp. 540–544, Oct. 1984: "Use of a Palatal Reservoir in Denture Patients with Xerostomia", Joseph A. Toljanic D.D.S. et al.,
The Journal of Prosthetic Dentistry, vol. 52, No. 5, Nov. 1984, pp. 710–715: "Artificial Saliva Reservoirs", A. Visink, D.M.D. et al.
Quintessence of Dental Technology, vol. 9, No. 6, Jun. 1985, pp. 355–358: Fabrication of an Artification Saliva Reservoir Denture System for Xerostomia Management, Joseph A. Toljanic, D.D.S. et al.
Proc. Finn, Dent. Soc., 1989, 85 No. 1, Department of Prosthetic Dentistry, University of Helsinki, Helsinki, Finland, pp. 47–50, "Treatment of Xerostomia Through Use of Dentures Containing Reservoirs of Saliva Substitute", Markhu Hirikangas et al.

Primary Examiner—Nicholas D. Lucchesi
(74) Attorney, Agent, or Firm—Pearne & Gordon LLP

(57) ABSTRACT

A reservoir system for delivering an active agent into an oral cavity over an extended delivery period includes a pair of rigid plastic containers, which each have a hollow interior space for containing the active agent and at least one opening for dispensing the active agent, and a flexible plastic appliance for securing the containers within the oral cavity at a desired location. The containers are located within chambers formed in opposite sides of the appliance. The container includes a molded plastic body having a size and shape suitable for comfortably retaining the container within the oral cavity for the extended delivery time. The body is generally oval and cabochon-shaped to comfortably fit in the vestibule between the teeth/gums and cheek of the patient and has a plurality of dimples for selectively forming venting and dispensing holes at desired locations. The appliance is custom molded to closely fit the patient. The reservoir system preferably includes a foraminous medium for holding and dispensing additional active agent at a desired treatment location within the oral cavity. The foraminous medium is preferably imbedded within the flexible plastic appliance and preferably located adjacent the palate of the patient.

14 Claims, 7 Drawing Sheets

U.S. PATENT DOCUMENTS

| | | | |
|---|---|---|---|
| 4,676,752 | 6/1987 | Lefkowitz | 433/229 |
| 4,715,368 | 12/1987 | George | 128/136 |
| 4,959,052 | 9/1990 | Cox | 604/77 |
| 4,968,251 * | 11/1990 | Darnell | 433/80 X |
| 5,248,310 | 9/1993 | Barclay et al. | 604/891.1 |
| 5,334,189 | 8/1994 | Wade | 604/890.1 |
| 5,356,291 | 10/1994 | Darnell | 433/216 |
| 5,409,017 | 4/1995 | Lowe | 128/848 |
| 5,575,654 | 11/1996 | Fontenot | 433/80 |
| 5,846,058 * | 12/1998 | Fischer | 433/80 X |

* cited by examiner

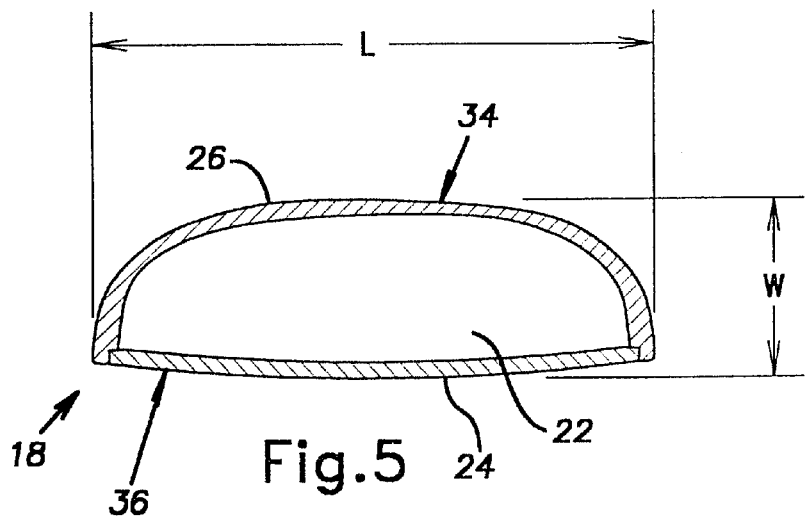
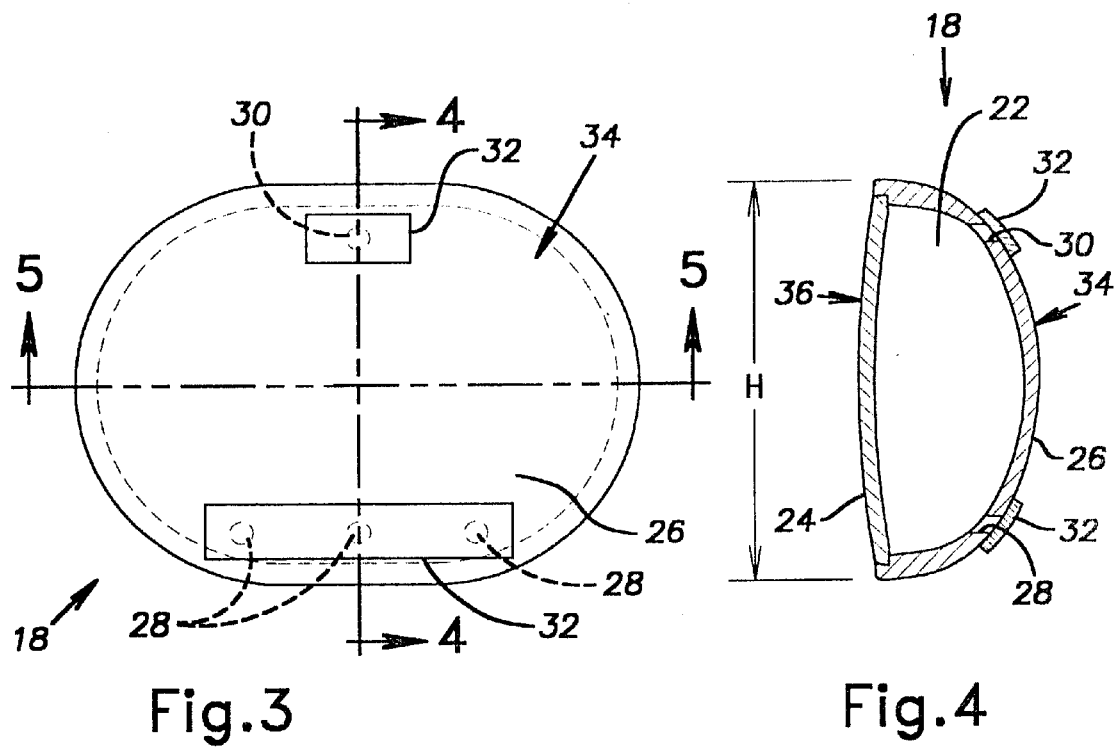

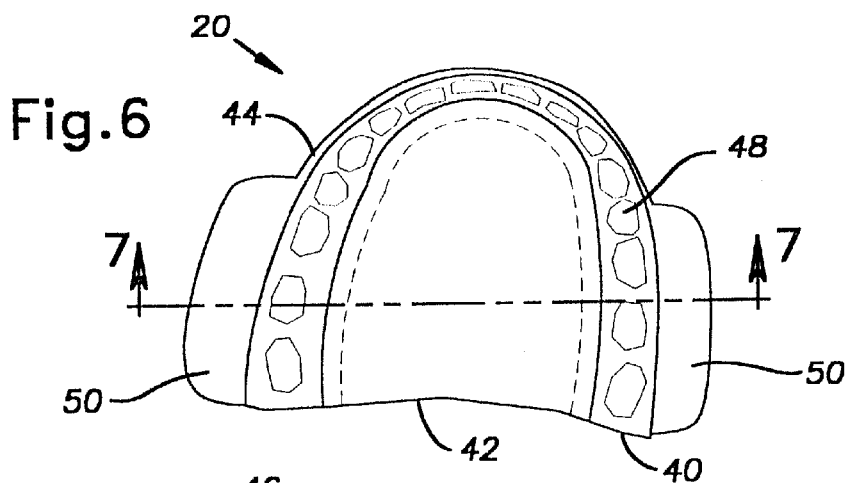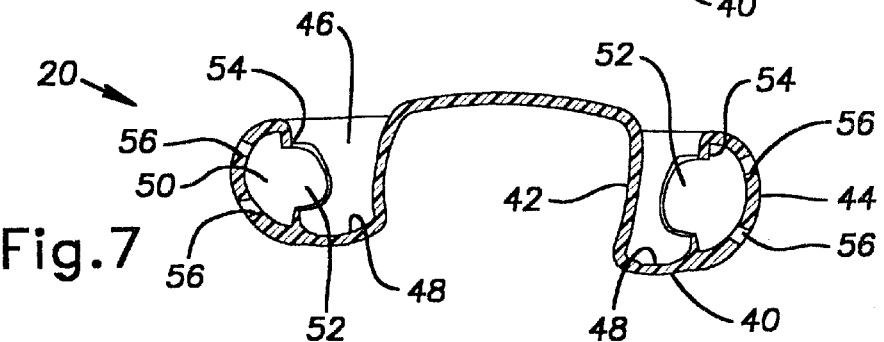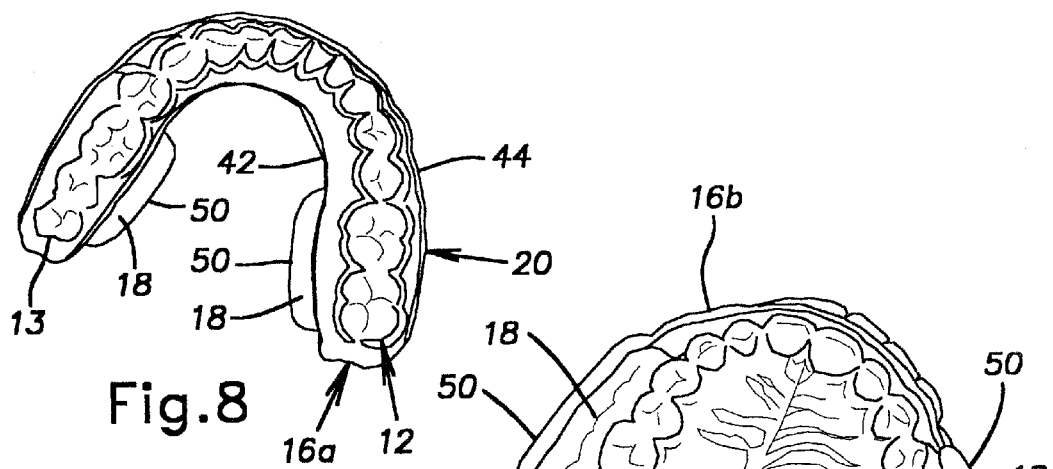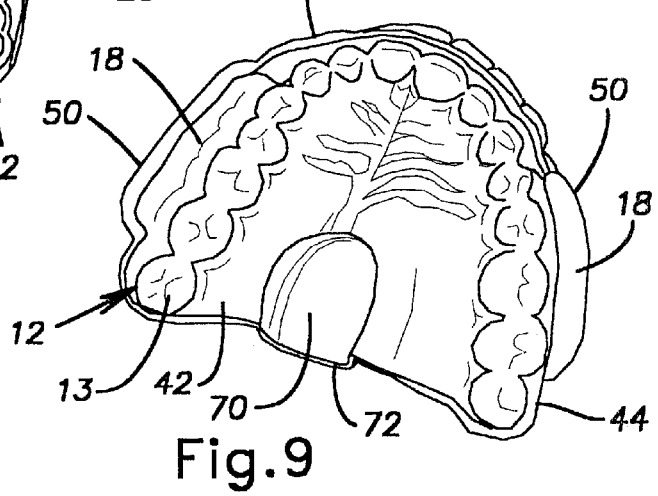

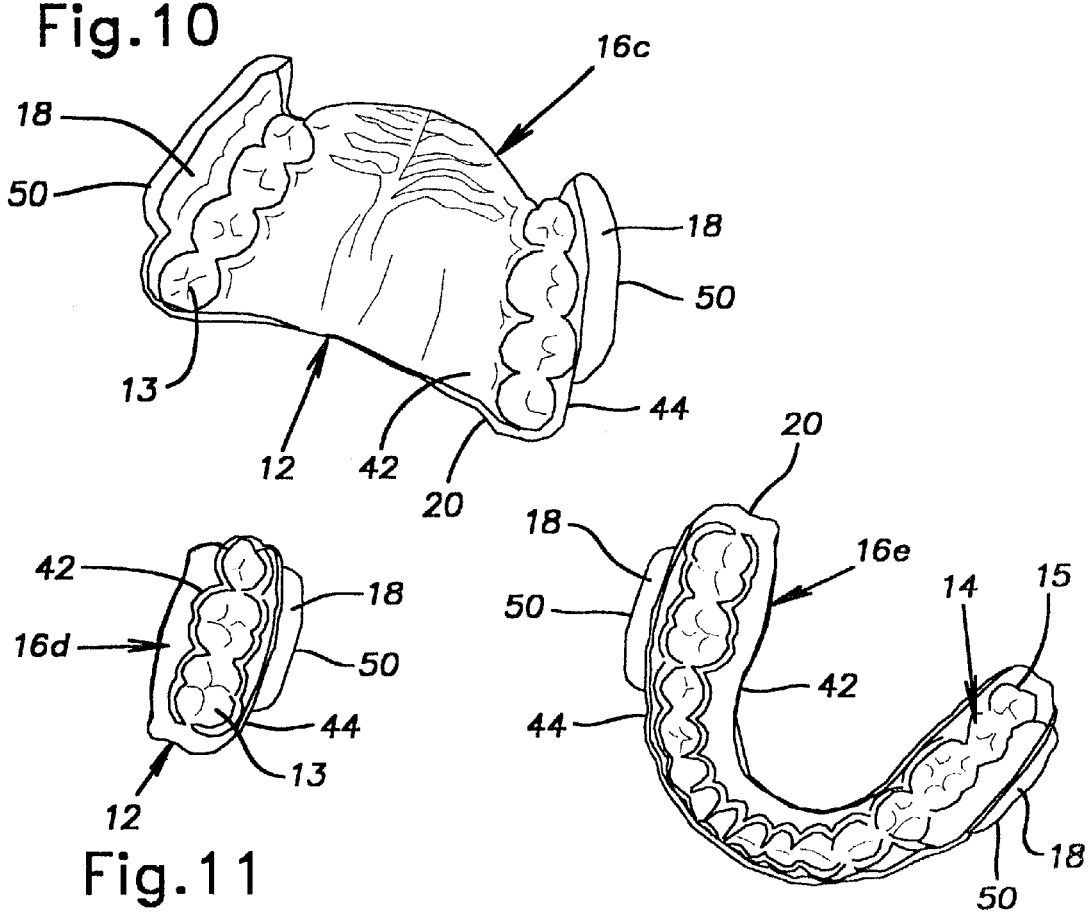
Fig. 10
Fig. 11
Fig. 12
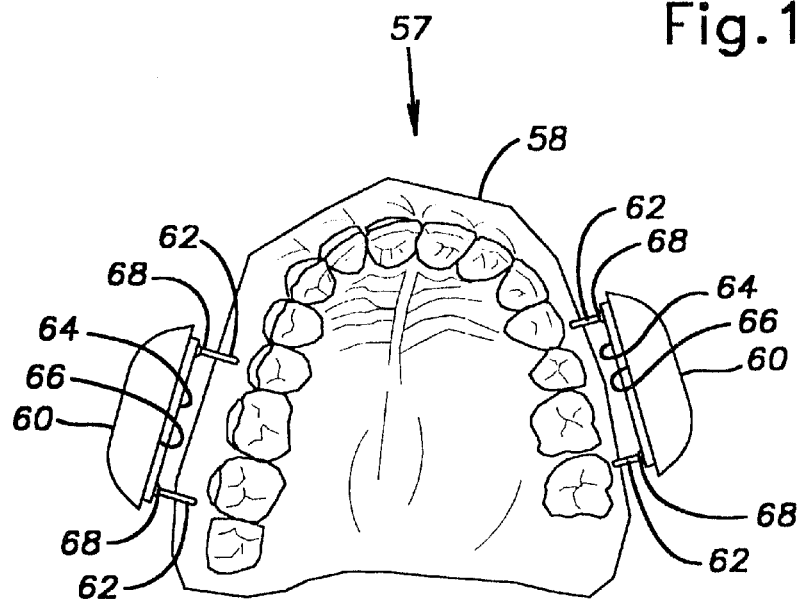
Fig. 13

MEDICAL RESERVOIR SYSTEM

This application is a continuation-in-part of U.S. patent application Ser. No. 08/924,800 filed on Sep. 5, 1997 now U.S. Pat No. 5,842,680.

BACKGROUND OF THE INVENTION

The present invention generally relates to reservoir systems for delivering agents into oral cavities of patients and, more particularly, to such systems which deliver controlled amounts of the agents over a prolonged period of time.

Many acute and chronic diseases which involve saliva glands can result in persistent xerostomia, that is, "dry mouth" or abnormal dryness of the mouth due to insufficient secretions. Because saliva has many important functions in the oral cavity, xerostomia can be uncomfortable and can lead to dehabilitating conditions. In many cases the condition cannot be treated curatively by the use of mechanical or chemical stimulants because of the lack of functioning saliva glands. The condition, however, can often be treated symptomatically by the use of saliva substitutes. The saliva substitutes are typically placed in the mouth by spraying, sucking, dripping, or pouring the artificial saliva into the mouth from a container which must be carried by the patient. The problem with this self administration is that there is a short duration of relief. The short duration requires the patient to keep the container continuously at hand and to frequently stop to wet the inside of their mouth, teeth, gums, tongue, throat, and anywhere else there are mucous tissues.

Several devices have been developed to improve or simplify delivery of the artificial saliva. One such device is a complete or partial maxillary denture having a palatal reservoir for storing a quantity of artificial saliva. The artificial saliva is drawn out of the reservoir when desired and the reservoir is refilled when needed. This solution has the problem of an increased palatal thickness which can cause heightened gag response, swallowing difficulties, and/ or alteration of the patients' speech, particularly those patients with low palatal vaults.

Another device is a complete or partial mandibular denture having a reservoir in each lingual flange below the posterior teeth. A saliva substitute is placed in the reservoirs and is dispensed when needed. This device has the problem of bulk and also has limited application because some patients do not and/or are unable to wear dentures. Additionally, the device does not have an adjustable control of the artificial saliva flow rate. It is noted that the device of first solution also has these same problems.

Devices have also been developed for delivering drugs or other beneficial agents into the oral cavity of a patient over a prolonged period of time such as, for example, an osmotic pump. Such devices typically have a bulk which interferes with speech and swallowing and may have edges which irritate and/or lacerate any mucus membranes in comes into contact with. Such devices however, like lozenges, typically have the problem of the natural tendency for the patient to suck or chew on the device which depletes the supply in a relatively short period of time. One solution has been to directly adhere or secure the devices to teeth or buccal tissues. Such invasive attachments can cause irritation and/ or difficulty in replenishing the supply as well as difficulty stabilizing the supply in place to prevent peeling, sliding, and detachment. Additionally, such devices do not hold a sufficient quantity of the beneficial agent to meet the needs of many applications. Such as, for example, treating xerostomia which requires delivery of the artificial saliva over a prolonged period of time.

Accordingly, there is a need in the art for an improved device which delivers an agent into the oral cavity of a patient over a prolonged period of time. It is preferable that the improved device holds a suitable and controllable supply of the agent yet is not bulky enough to affect the user's speech or to be readily visible. Additionally, it is preferable that the device adequately secures the agent yet does not cause irritation and is easy for the user to securely insert and remove from their mouth. Furthermore, it is preferable that the device can be used by patients with and without dentures.

BRIEF SUMMARY OF THE INVENTION

The present invention provides a novel and satisfactory reservoir system for delivering an active agent into an oral cavity over an extended delivery period which overcomes at least some of the above-noted problems of the related art. According to the invention, the reservoir system includes at least one container having a hollow interior space for containing the active agent and at least one opening for dispensing the active agent from the interior space and an appliance for securing the container within the oral cavity at a desired location. The container is located within the chamber of the appliance.

According to another aspect of the invention, the container includes a body having a size and shape suitable for comfortably retaining the body in the oral cavity for the extended delivery period, a hollow interior space for holding the active agent, and at least one opening for dispensing the active agent from the interior space. Preferably, the body is generally cabochon-shaped to comfortably fit within the vestibule between the teeth, gums and cheek of the patient. Preferably, the container has a plurality of dimples for selectively forming venting and dispensing holes at desired locations.

According to yet another aspect of the invention, a reservoir system includes a foraminous medium for holding and dispensing the active agent and an appliance for holding the foraminous medium at a desired treatment location within the oral cavity. The foraminous medium is secured to, and preferably imbedded within a molded plastic appliance. Preferably, the foraminous medium is located adjacent the palate of the patent and is sized to hold a relatively large volume of the active agent so that the containers can be reduced in size.

BRIEF DESCRIPTION OF THE SEVERAL VIEWS OF THE DRAWINGS

These and further features of the present invention will be apparent with reference to the following description and drawings, wherein:

FIG. 3 is an outer-side elevational view of a container of the medical reservoir system of FIG. 1;

FIG. 4 is a cross-sectional view taken along line 4—4 of FIG. 3;

FIG. 5 is a cross-sectional view taken along line 5—5 of FIG. 3;

FIG. 6 is a top plan view of a stabilizing appliance of the medical reservoir system of FIG. 1;

FIG. 7 is a cross-sectional view taken along line 7—7 of FIG. 6;

FIG. 8 is a diagrammatic view of the maxilla with a medical reservoir system according to a second embodiment of the present invention;

FIG. 9 is a diagrammatic view of the maxilla with a medical reservoir system according to a third embodiment of the present invention;

FIG. 10 is a diagrammatic view of a portion of the maxilla with a medical reservoir system according to a fourth embodiment of the present invention;

FIG. 11 is a diagrammatic view of a portion of the maxilla with a medical reservoir system according to a fifth embodiment of the present invention;

FIG. 12 is a diagrammatic view of the mandible with a medical reservoir system according to a sixth embodiment of the present invention;

FIG. 13 is a plan view of tooling for forming the maxillary stabilizing appliance of FIG. 6 and 7;

DETAILED DESCRIPTION OF PREFERRED EMBODIMENTS

Figure 1:
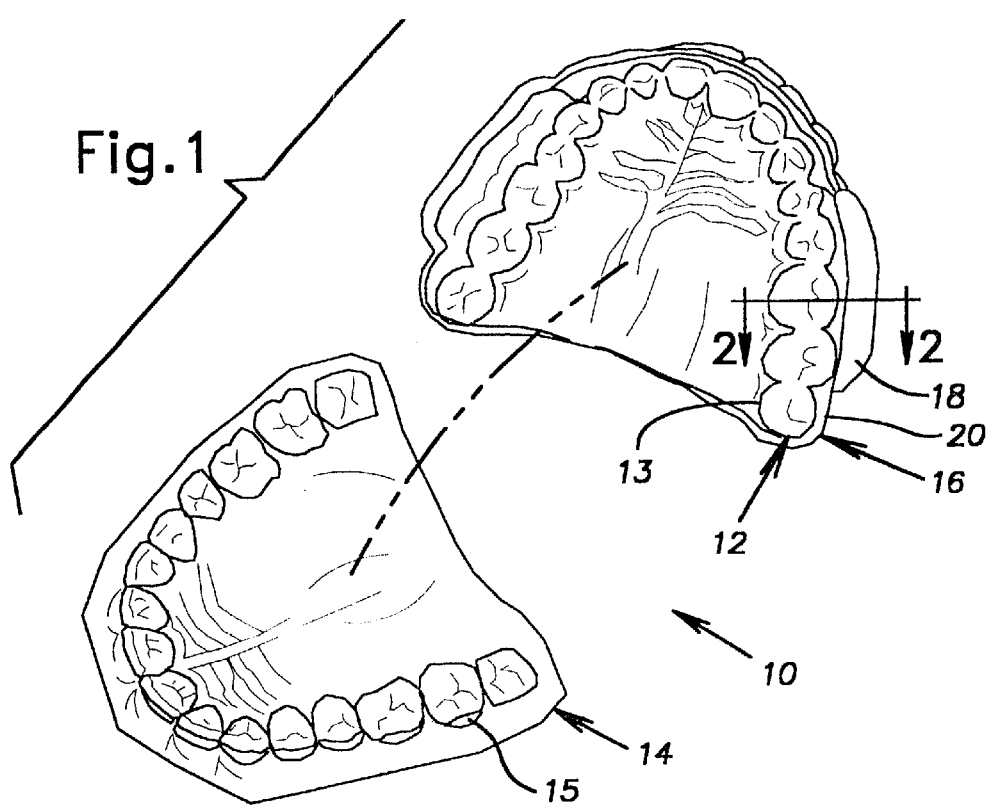
FIG. 1 is a diagrammatic view of an oral cavity of a patient with a medical reservoir system according to the present invention secured therein.
Figure 2:
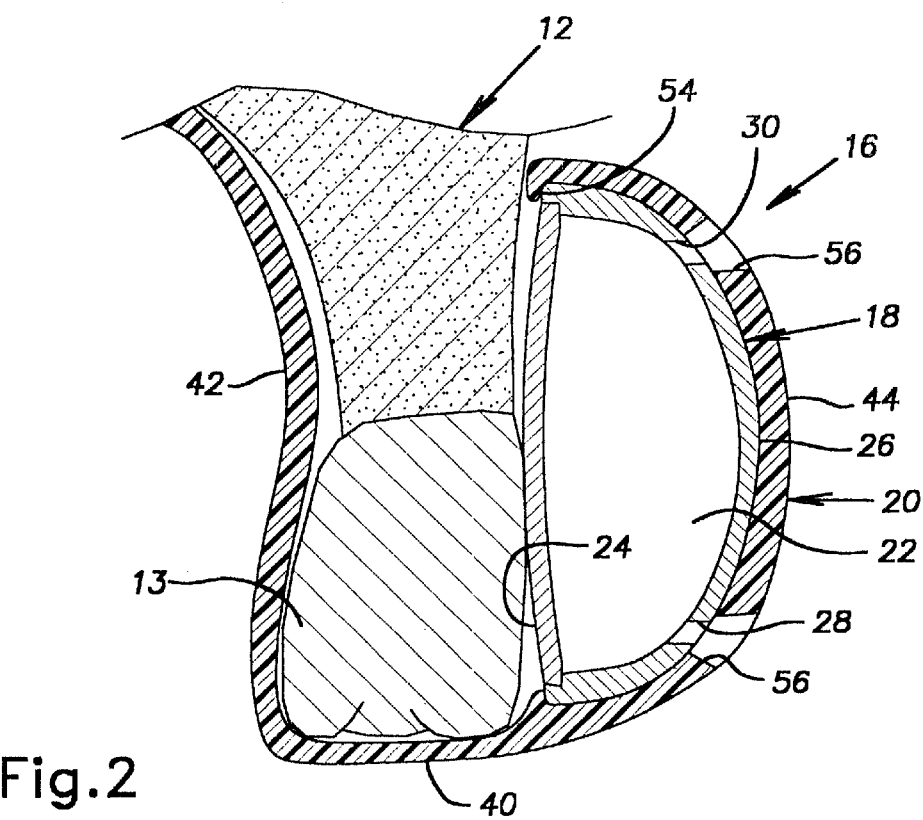
FIG. 2 is a cross-sectional view taken along line 2—2 of FIG. 1.

FIGS. 1 and 2 diagrammatically illustrate an oral cavity 10 of a patient including a maxilla or upper jaw 12 with teeth 13 and a mandible or lower jaw 14 with teeth 15. A medical reservoir system 16 according to the present invention is located within the oral cavity 10 for intra-orally delivering an active agent over a prolonged period of time. The reservoir system includes containers 18 for holding and distributing the active agent over a desired prolonged period of time and a holding or stabilizing appliance 20 for securing the containers 18 in desired locations within the oral cavity 10.

The term "active agent", as used within the specification and accompanying claims, includes any beneficial agent or compound that can be delivered from the medical reservoir system 16 into the oral cavity 10 to produce a beneficial result. Additionally, the term "agent" includes "drug", and the term "drug" includes any physiologically or pharmacologically active substance that produces a local or systemic effect when administered into the oral cavity. The term "physiologically", as used herein, denotes the administration of a drug to produce normal levels and functions. The term "pharmacologically", as used herein, denotes variations in response to amount of drug administered.

The preferred active agent of the illustrated embodiment is an artificial saliva such as, for example, SALIVART®, available from the Gebauer Company, Cleveland Ohio. Other active agents which may be deliverable from the medical reservoir system 16 into the oral cavity 10 include inorganic and organic drugs, antibiotics, central nervous system drugs, depressants, hypnotics, sedatives, psychic energizers, tranquilizers, anticonvulsants, muscle relaxants, analgesics, anti-inflammatories, local anesthetics, muscle contractants, anti-microbials, anti-fungals, anti-malarials, hormonal agents, contraceptives, sympathomimetics, diuretics, anti-parasitics, nedplastics, hypoglycemics, ophthalmics, electrolytes, diagnostic agents, and cardiovascular drugs.

The terms "prolonged or extended period of time" and "extended delivery period", as used within the specification and accompanying claims, generally refer to periods greater than a few minutes and typically in the range of about 0.5 hours to about 12 hours. For the illustrated embodiment regarding the delivery of artificial saliva into the oral cavity 10, the extended delivery time is preferably within the range of about 1 hour to about 8 hours.

The term "container", as used within the present specification and accompanying claims, includes any device or receptacle which holds or contains a quantity of the active agent such as, for example, carpules or capsules. Additionally, the term "container" includes any device or receptacle which holds the active agent with a rigid or pliable, soluble or insoluble, permeable or impermeable layer of material.

The active agent may itself be provided in a time-release form such as a tablet, capsule, pastille, lozenge, pill or other construction that discharges or releases the active agent over a desired time period. For example, an elongate tablet of transverse layers or a pill of concentric spherical layers may dissolve within the container in response to a dispensing stimulant such as saliva to provide timed discharge of the active agent. In such arrangement, saliva may enter the container and exit the container with dissolved active agent through the single dispensing opening or a number of container openings may be provided with or without a preselected flow direction.

As best shown in FIGS. 3–5, each illustrated container 18 forms a hollow interior cavity or space 22 for holding and distributing the active agent. The active agent, held within the container 18, can be in various forms such as, for example, liquids, gels, plasmas, and solids. It is noted, however, that a solid active agent, such as a time release tablet/capsule or a lozenge, can be held either in the container 18 or directly in the appliance 20 without the container 18. Because the container 18 remains within the oral cavity 10 of the patient for an extended delivery period, each container 18 has an exterior shape and size suitable for comfortably fitting within the mouth between the cheek and teeth/gums. The container 18 preferably is cushion or oval-shaped as best shown in FIG. 3. The container 18 is also preferably cabochon-shaped in cross-section, that is, the container 18 has a generally flat inner side 24 and a generally rounded or convex outer side 26 as best shown in FIGS. 4 and 5. As shown in FIGS. 4 and 5, the generally flat inner surface 24 preferably has a slight curvature in each direction. The cabochon-shape enables the generally flat inner side 24 of the container 18 to closely fit against the outer surface of the teeth and gums and the convex outer side 26 to closely fit against the inner surface of the cheek.

The hollow interior space 22 of the container 18 must be sized for holding a suitable volume of the active agent for delivery over the extended delivery period. For artificial saliva, the container 18 preferably has a volume of about 2 to about 5 cm³ and more preferably has a volume of about 3 cm³. It is believed that the container 18 fits most comfortably in the mouth of a human with an aspect or side ratio, that is a ratio of length/height (L/H), in the range of about 1.2 to about 3. In addition, it is believed that the container 18 fits most comfortably in the vestibule between the cheek and the teeth and gums of a human with a width W of about 10 mm or less. Furthermore, the container 18 is preferably of a low profile, that is, the length L and the height H are each preferably larger than the width W. A container 18 obtaining particularly good results has a length L of about 31 mm, a height H of about 23 mm, and width W of about 10 mm which forms a suitable volume for the active agent of about 3 cm³ and fits comfortably within the mouth of an adult for the prolonged period of time. For children and some adults having a relatively small vestibule between the cheek and the teeth/gums, it may be necessary to reduce the width W of the container 18.

The container 18 has three dispensing holes 28 and a venting hole 30 formed therein. The dispensing holes 28 horizontally extend through the outer side 26 of the container 18 generally near the bottom of the container 18. Each dispensing hole 28 preferably has a diameter of about 1/32 inch to about 1/8 inch, and more preferably about 3/64 inch. Typically, as the viscosity of the active agent increases, the required diameter of the dispensing holes 28 increases. The venting hole 30 horizontally extends through the outer side 26 of the container 18 near the top of the container 18. The venting hole 30 also preferably has a diameter of about 1/32 inch to about 1/8 inch. The size, quantity and location, of the holes 28, 30 are selected to obtain a desired flow rate over a desired extended delivery period. Therefore, the container 18 can have a larger or smaller quantity of dispensing and/or venting holes 28, 30, the holes 28, 30 can be located in other locations, and/or the holes 28, 30 can have other diameters depending on the active agent, the desired flow rate, and the desired extended delivery period. It is also noted that the container 18 may require a separate filling hole (not specifically shown) at any suitable location if the dispensing and venting holes 28, 30 do not have a suitable diameter, typically a diameter of at least 1/16 inch, for filling the container 18 with the active agent.

The dispensing holes 28 are preferably located so that the active agent is dispensed whether the patient's head is upright or laying down. To this end, it is preferable that at least one dispensing hole 28 is located at the rear bottom portion of the container 18 as best shown in FIG. 3. It is also preferable that another dispensing hole 28 is symmetrically located at the front bottom portion of the container 18 so that the container 18 can be interchangeably utilized in either the left or right side of the patient's mouth.

The holes 28, 30 are covered with a removable tape 32 having a face stock for closing the holes 28, 30 and an adhesive for securing the face stock to the container 18. Preferably, instructions can be printed directly on the removable tape 32. The removable tape 32 is also preferably in compliance with FDA regulations for direct food contact. A removable tape which provides adequate results is available from Visual Marking Systems, Inc., Twinsburg, Ohio and has a semigloss paper face stock and a TDF 900 general purpose latex adhesive. The removable tape 32 is placed over the holes 28, 30 to retain the active agent in the container 18 during shipping and handling of the container 18. The tape 32 is removed, to open the holes 28, 30, prior to insertion of the medical reservoir system 16 into the mouth as described in more detail hereafter. The tape 32 can be advantageously left on some of the dispensing holes 28 in order to adjust or control the flow rate of the active agent from the container 18.

The container 18 of the illustrated embodiment is constructed by injection molding a main body 34, primarily forming the generally convex outer surface 26 of the container 18, and a cover 36, primarily forming the generally flat inner surface 24 of the container 18. The main body has a generally open inner side which is closed by the cover 36. A seat 38 is formed around the perimeter of the open inner side for receiving the cover 36 to close the main body 34 and form the hollow interior space 22. The cover 36 is attached or secured to the main body 34 in any suitable manner which seals the joint therebetween such as, for example, sonic welding. Alternatively, the container 18 can be formed in other manners such as, for example, blow molding a single-piece hollow body.

The container 18 is preferably constructed from a moldable plastic in compliance with FDA regulations for direct food contact such as, for example, high density polyethylene (HDPE), polypropylene copolymer, or polyamide (nylon 66). A suitable HDPE is Dow HDPE 10462N manufactured by Dow Plastics. A suitable polypropylene copolymer is Pro-fax SB-786 manufactured by Montell Polyolefins. A suitable polyamide (nylon 66) is Zytel 101 NC010 (cond) manufactured by Dupont Engineering Polymers. The material is preferably transparent or translucent so that the patient can visually check the quantity of the active agent in the container 18. To this end, the active agent can also be colored to be more easily seen through the wall of the container 18. The plastic material also preferably has the required rigidity to prevent collapsing upon sucking by the patient.

The stabilizing appliance 20 of the illustrated embodiment is a maxillary appliance and is preferably custom fitted to each patient's oral cavity and teeth/gums profile. As best shown in FIGS. 6 and 7, the stabilizing appliance 20 has a generally horizontal main wall 40, an inner or palatal flange 42 upwardly extending from an inner edge of the main wall 40, and an outer or buccal flange 44 upwardly extending from an outer edge of the main wall 40. The main wall 40 and the flanges 42, 44 cooperate to form a generally U-shaped channel 46 adapted to firmly but releasably connect or secure the appliance 20 to the maxillary teeth 13 of the patient. On the upper side of the main wall 40, within the channel 46, are custom molded depressions 48 matching the user's maxillary teeth 13. The palatal and buccal flanges 42, 44 also have custom molded shapes which closely match the patient's teeth/gums profile. The palatal flange 42 is preferably sized and shaped with a central portion which fully extends across the palate of the patient (best shown in FIG. 7). The buccal flange 44 is preferably sized and shaped to extend over the maxillary teeth 13 and at least a portion of the gums above the maxillary teeth 13 (best shown in FIG. 2). The appliance 20 preferably has a nominal wall or flange thickness in the range about 1 mm to about 3 mm.

Formed within the buccal flange 44 are a pair of cavities or chambers 50 for holding the containers 18. The chambers 50 are located on opposite sides of the appliance 20 to locate the containers 18 between the cheek and the teeth/gums on opposite sides of the mouth. The chambers 50 are preferably sized and shaped to closely match the containers 18. The chambers 50 preferably have an opening 50 which opens into the channel 46 and a lip 52 formed about the periphery of the opening to removably retain or secure the containers 18 within the chambers 50. The appliance 20 is preferably formed of a resiliently flexible material so that the containers 18 can be easily snapped into and out of the chambers 50.

The chambers 50 are also preferably provided with suitable openings 56 which cooperate with the dispensing and venting holes 28, 30 of the containers 18 so that active agent can directly flow out of the appliance 20. It is noted, however, that the openings 56 are not provided when it is desirable to at least partially retain the active agent within the appliance 20.

The appliance 20 is constructed from an intraorally acceptable, flexible, and moldable plastic such as, for example, polyethylene or ethylene vinylacetate. A suitable polyethylene is COPYPLAST manufactured by Cadillac Plastics. A suitable ethylene vinylacetate is BIOPLAST manufactured by Cadillac Plastics. The material is preferably transparent or translucent so that it is difficult to see the appliance 20 when worn in the mouth of the patient.

FIG. 13 illustrates tooling 57 for forming the stabilizing appliance 20 of FIGS. 6 and 7 which includes a stone model 58 and a pair of container dies 60. It is noted that the number of container dies 60 matches the number of containers 18 to be held by the stabilizing appliance 20, therefore the tooling 57 will have a different quantity of container dies 60 when a different number of containers 18 are to be held by the stabilizing appliance 20. To form the appliance 20, a dentist takes a high and deep impression of the patient's maxilla which extends deep into the vestibules between the teeth/gums and the cheek. The dentist then casts the stone model 58 from the impression, identifies the preferred location of the containers 18 thereon, and ships the model 58 to a suitable lab. The locations of the containers 18 are selected by the dentist because vestibules vary from patient to patient, some being shallow and some being deep, and therefore the preferred locations of the containers 18 vary from patient to patient.

The container dies 60 are shaped to closely match the containers 18 and have a pair of spaced apart prongs or pins 62 extending from the inner generally flat side 64. The dies 60 are slightly larger than the containers 18 to account for shrinkage of the appliance material and have undercuts 66 to form the lips 54 described hereinbefore. The dies 60 are formed from any suitable material such as aluminum or other metal. The pins 62 preferably have a joint or hinge 68 located at the inner side 64 of the container die 64 so that the angles between the dies 60 and the pins 62 can be adjusted.

When the lab receives the stone model 58 from the dentist with the preferred location of the containers 18 marked thereon, a pair of spaced-apart and parallel holes are drilled on each side of the model 58 for receiving the pins 62 of the dies 60. Preferably, the pairs of holes are drilled with a drill press having parallel drills. The pins 62 of the dies 60 are inserted into the holes, the container dies 60 are tilted to a desired angle with the hinges 68, and the pins 62 are secured in place by any suitable manner such as by an adhesive.

Once the tooling 57 is completed, the stabilizing appliance 20 is preferably formed by placing a sheet of plastic material over the tooling 57 and placing the material and tooling 57 into a molding machine. The molding machine heats the plastic material and applies vacuum or air pressure on the plastic material to form the plastic material directly onto the model 58 and container dies 60 guaranteeing a perfect fit with the patient. The appliance 20 is then removed from the tooling 57, excess plastic material is trimmed off, the openings 56 are formed if required, and the appliance 20 is returned to the dentist for delivery to the patient.

To use the medical reservoir system 16, the patient removes the removable tape 32 from the holes 28, 30 of the containers 18, containing the desired active agent such as artificial saliva, to open the holes 28, 30. It is noted that it may be desirable to remove the tape 32 from all or only some of the holes 28, 30, depending on the desired flow rate. It is also noted that it may be desirable to open a different number of holes on each of the containers, to obtain different flow rates at different locations within the mouth. The containers 18 are then resiliently snapped into the chambers 50 of the stabilizing appliance 20 where they are secured in place by the lips 54. The stabilizing appliance 20 is inserted into the mouth onto the maxilla 12 and is firmly but releasably secured to the maxillary teeth 13 of the patient.

As best shown in FIGS. 1 and 2, the containers 18 are secured in the vestibules between the cheeks and teeth/gums of the patient generally adjacent the first and second bi-cuspids and the first and second molars. The active agent downwardly flows, under the influence of gravity, out of the containers 18 through the dispensing holes 28, out of the appliance 20 through the openings 56, and into the oral cavity 10 of the patient. The active agent continues to flow at the selected rate, controlled by the size and number of the holes 28, 30, over the prolonged period of delivery. Due to the shape, size, and location of the containers 18, the containers can comfortably remain within the oral cavity 10 of the patient for the prolonged delivery time. Additionally, the medical reservoir system 16 does not impact the speech of the patient and is nearly visibly undetectable.

Once the containers 18 are empty, the appliance 20 is removed from the oral cavity 10, the empty containers 18 are snapped-out of the appliance 20, and the above described procedure is repeated. It can be seen from the above description that the reservoir system of the present invention provides an improved device which controllably delivers an active agent into the oral cavity of a patient over an extended delivery period and is easy for the patient to insert and remove from their mouth. It can also be seen that the present invention provides an improved device which holds a suitable and controllable supply of the agent yet does not affect the user's speech and swallowing, is not readily visible, and can be used by patients with and without dentures.

FIG. 8 diagrammatically illustrates the maxilla 12 with a medical reservoir system 16a according to a second embodiment of the present invention. The medical reservoir system 16a is similar to the system 16 discussed above and like reference numbers are used for like structure. The medical reservoir system 16a illustrates that the containers 18 can be secured at other locations in the oral cavity within the scope of the present invention. In the second embodiment, the chambers 50 of the appliance 20 are located on the palatal flange 42 instead of the buccal flange 44. Therefore, the containers 18 are located at opposite sides of the palate against the inner side of the maxillary teeth 13. Preferably, the palatal flange 42 does not have a central portion which fully extends across the palate. It is noted that the containers 18 should be sized, typically smaller than the containers 18 of the first embodiment, in order to avoid impact on patient's speech.

FIG. 9 diagrammatically illustrates the maxilla 12 with a medical reservoir system 16b according to a third embodiment of the present invention. The medical reservoir system 16b is similar to the systems discussed above and like reference numbers are used for like structure. The medical reservoir system 16b illustrates that additional containers 70 can be utilized and that containers can be located at the palate within the scope of the present invention. In the third embodiment, an additional chamber 72 of the appliance 20 is located on the palatal flange 42. Therefore, the additional container 70 is located at the palate and is held against the palate by the palatal flange 42 of the appliance 20. It is noted that the additional container 70 at the palate can be used with or without the other containers 18 and the other containers 18 can be located at other locations.

FIG. 10 diagrammatically illustrates a portion of the maxilla 12 with a medical reservoir system 16c according to a fourth embodiment of the present invention. The medical reservoir system 16c is similar to the systems discussed above and like reference numbers are used for like structure. The medical reservoir system 16c illustrates that the appliance 20 can be a partial appliance. In the fourth embodiment, the appliance 20 is formed to cover only a portion of the posterior maxillary teeth 13. In the illustrated embodiment, only the molars and the bicuspids are covered by the appliance 20 but other combinations of teeth can be used within the scope of the present invention. It is noted that the appliance 20 may require relatively stiffer or relatively thicker plastic material. The appliance 20 enables the medical reservoir system 16c to be less visible when worn by the patient and enables the medical reservoir system 16c to be used by patients having missing teeth.

FIG. 11 diagrammatically illustrates a portion of the maxilla 12 with a medical reservoir system 16d according to a fifth embodiment of the present invention. The medical reservoir system 16d is similar to the systems discussed above and like reference numbers are used for like structure. The medical reservoir system 16d illustrates that the appliance 20 can be limited to covering only a few of the maxillary teeth 13. In the illustrated embodiment, only two molars and a bicuspid are covered by the appliance 20 but other quantities and combinations of teeth 13 can be utilized within the scope of the present invention. It is noted that the appliance 20 may require wires or clasps for securing the appliance to the teeth 13. Like the fourth embodiment, the appliance 20 enables the medical reservoir system 16d to be less visible when worn by the patient and enables the medical reservoir system 16d to be used by patients having missing teeth.

FIG. 12 diagrammatically illustrates the mandible 14, mandibular teeth 15, and inner cheek structure with a medical reservoir system 16e according to a sixth embodiment of the present invention. The medical reservoir system 16e is similar to the systems discussed above and like reference numbers are used for like structure. The medical reservoir system 16e illustrates that the appliance 20 can be a mandibular appliance. In the sixth embodiment, the chambers 50 of the appliance 20 are located within the buccal flange 44. Therefore, the containers 18 are located at opposite sides of the mouth between the teeth/gums and the cheek. The inner or lingual flange 42 does not have a central portion which fully extends across the appliance 20 so that a suitable opening for the tongue is provided.

Figure 14:
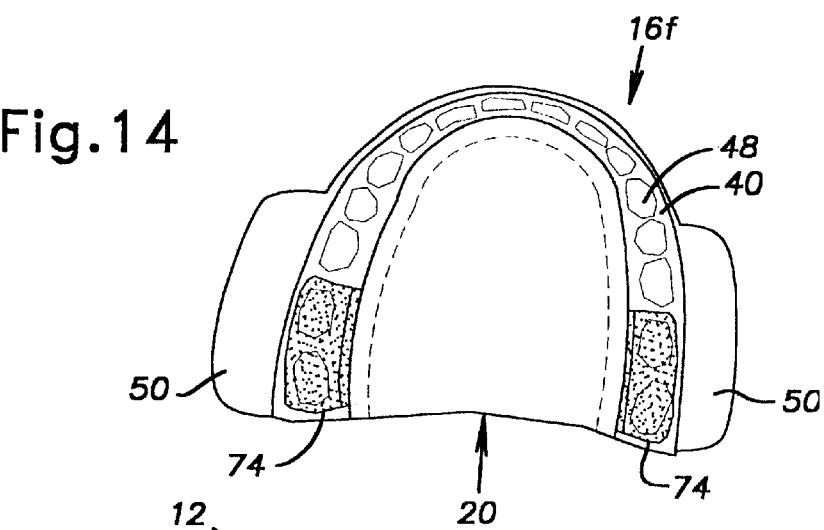
FIG. 14 is a plan view of medical reservoir system according to a seventh embodiment of the present invention.
Figure 15:
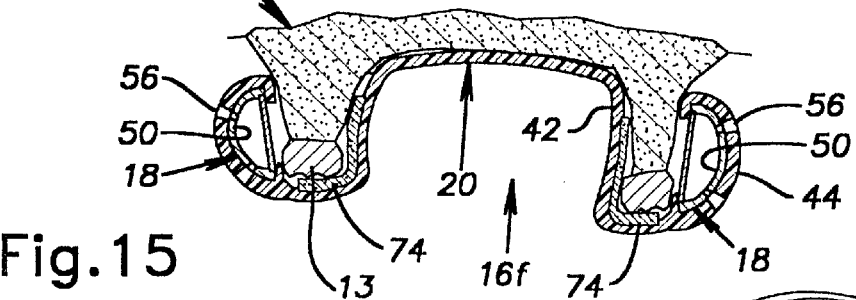
FIG. 15 is a diagrammatic view in cross-section of the medical reservoir system of FIG. 14 secured to a patient's maxilla.

FIGS. 14 and 15 illustrate a medical reservoir system 16f according to a seventh embodiment of the present invention. The medical reservoir system 16f is similar to the systems discussed above and like reference numbers are used for like structure. The medical reservoir system 16f illustrates that a foraminous medium 74 can be used to hold and dispense the active agent or an additional active agent. The term "foraminous medium", as used within the specification and accompanying claims, includes any fibrous, porous, or capillary-type medium which is capable of holding the active agent such as, for example, cotton, sponge, or foam. The foraminous medium can be of any intraorally acceptable material such as, for example, a polyester and polyurethane foam.

The foraminous medium 74 is supplied with the active agent, such as by pouring or spraying, prior to inserting the appliance 20 into the patient's mouth. The foraminous medium 74 is easily replenished with a supply of the active agent whenever it is necessary.

The foraminous medium 74 is particularly useful in applications where it is desirable to have a supply of the active agent directly at a specific treatment area. One application, for example, is the administration of an antibacterial agent, such as Chlorhexidine, or an antifungal agent, such as Nystatin, in the treatment of periodontal disease and/or yeast infections. The foraminous medium 74 provides a prolonged release of an effective concentration of the active agent directly at the diseased sites so that the active agent penetrates even deep pockets. By having both the foraminous medium 74 and the containers 18, both an artificial saliva and a antibacterial agent can be dispensed within the cavity to treat both xerostomia and periodontal disease, which is often brought on by xerostomia.

The foraminous medium 74 is preferably secured to the appliance 20 by imbedding the medium 74 directly into the surface of the plastic material of the appliance 20. The appliance 20 is formed in the same manner as described hereinbefore except that the holding and dispensing medium 20 is placed on the stone model 13 (FIG. 13), at the area to be treated, prior to placing the plastic material of the appliance 20 over the stone model 58. The foraminous medium 74 is preferably tacked to the stone model 58 with an adhesive wax to prevent movement when pressure is applied by the molding machine. Preferably, the foraminous medium 74 is heat compressed along edges which contact the appliance 20 so that the edges are denser to provide a better bond to the appliance 20. The appliance 20 is then formed in the molding machine as described hereinbefore.

In the illustrated embodiment, the foraminous medium 74 is located on the upper side of the main wall 40 and the inner side of the palatal flange 42 within the appliance channel 46 and is also located adjacent two of the molars on each side of the appliance 20. It is noted, however, that the foraminous medium 74 can be alternatively or additionally provided at any surface of the appliance 20 and adjacent any other or number of teeth and gums desired. The foraminous medium 74 is preferably customized to match and cover all locations where infection exists within the oral cavity. Therefore, the foraminous medium 74 can cover any portion or all of the surfaces of the teeth and gums. The foraminous medium 74 can also cover any or all of the anterior teeth, any or all of the posterior teeth, or any combination thereof.

Figure 16:
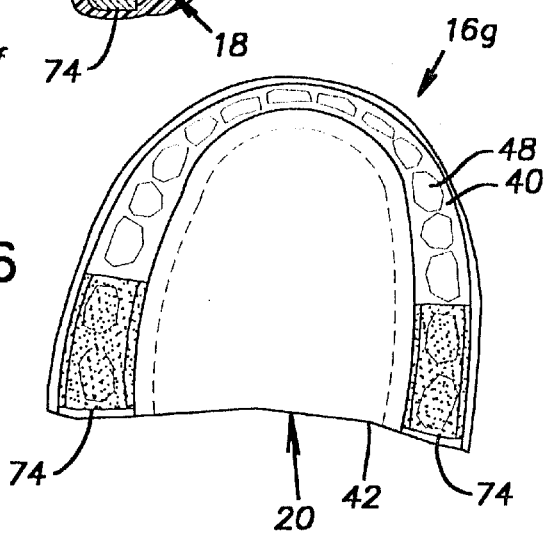
FIG. 16 is a plan view of medical reservoir system according to a eighth embodiment of the present invention.
Figure 17:
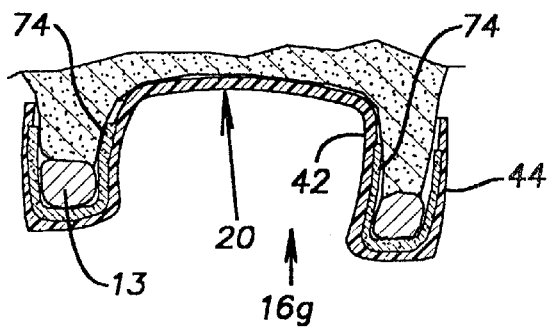
FIG. 17 is a diagrammatic view in cross-section of the medical reservoir system of FIG. 16 secured to a patient's maxilla.

FIGS. 16 and 17 illustrate a medical reservoir system 16g according to an eighth embodiment of the present invention. The medical reservoir system 16g is similar to the systems discussed above and like reference numbers are used for like structure. The medical reservoir system 16g illustrates that the foraminous medium 74 can be used to hold and dispense the active agent with an appliance 20 not having the hereinbefore described chambers 50 and containers 18.

In the illustrated embodiment, the foraminous medium 74 is located on the upper side of the main wall 40, the inside of the palatal flange 42, and the inside of the buccal flange 44. Therefore, the foraminous medium 74 is a "full liner", that is, the foraminous material generally covers the entire cross-section of the appliance channel 46. It is noted, however, that the foraminous medium 74 can be alternatively or additionally provided at any surface of the appliance 20 which is desired as discussed above.

Figure 20:
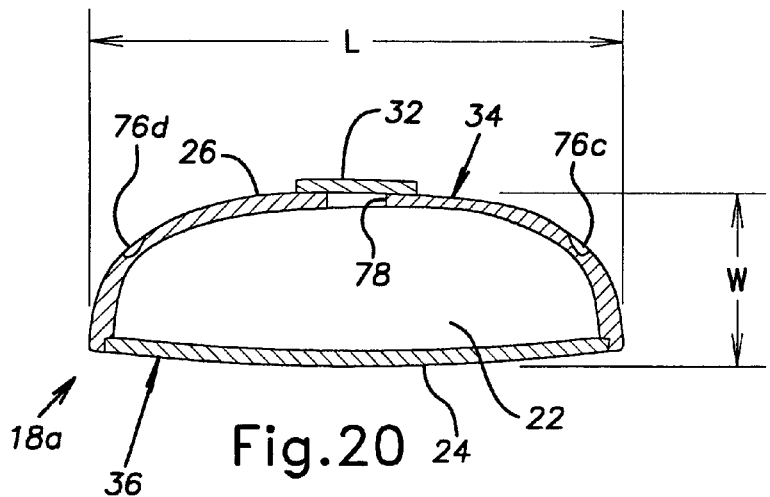
FIG. 20 is a cross-sectional view taken along line 20—20 of FIG. 18.
Figures 18, 19:
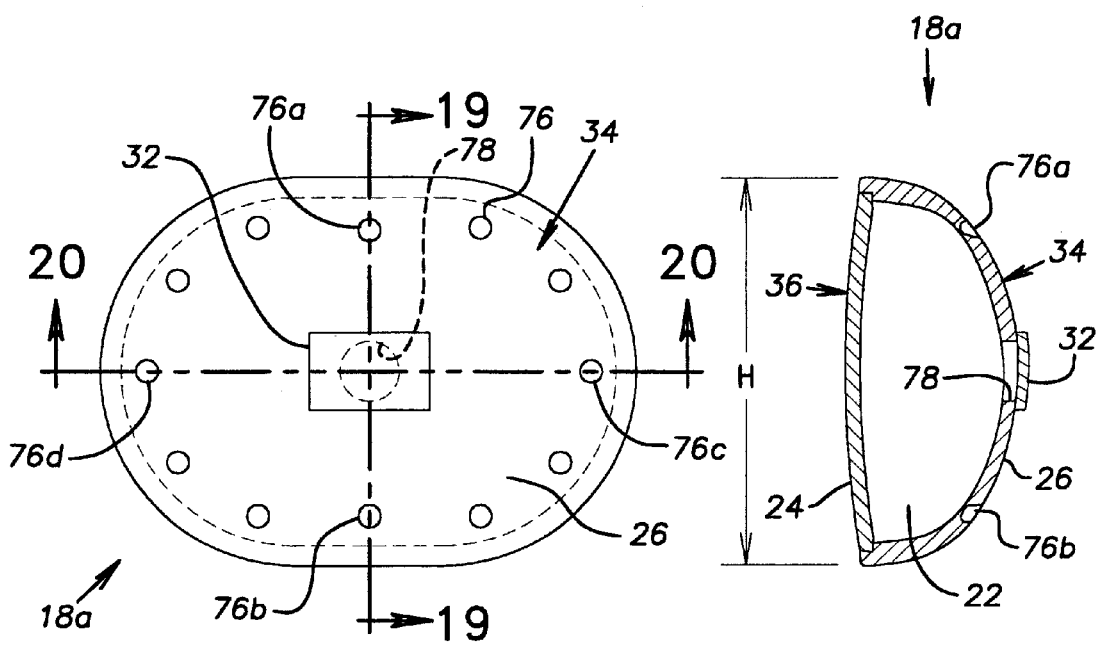
FIG. 18 is an outer-side elevational view of another container according to the present invention.
FIG. 19 is a cross-sectional view taken along line 19—19 of FIG. 18.

FIGS. 18–20 illustrate a second embodiment of a container 18a according to the present invention. The container 18a is substantially similar to the container 18 described in detail hereinabove except as noted hereinbelow. Note that like references numbers have been used to indicate like structure. The container 18 has a plurality of dimples 76 for forming dispensing and venting holes. The dimples 76 form areas having a relatively thin wall thickness which can be easily pierced by a piercing tool to form dispensing and venting holes in various quantities and locations. Preferably, the dimples 76 are located on the exterior surface of the container 18a so that they act as a guide for the piercing tool. The dimples 76, however, can alternatively be located on the interior surface of the container 18a as long as areas of relatively thin wall thickness are formed.

In the illustrated embodiment, the dimples 76 horizontally extend partially through the outer side 26 of the container 18a around the entire periphery of the outer side 26. Preferably, there are about twelve spaced apart dimples 76. It is noted, however, that the container 18a can have a larger or smaller quantity of dimples 76 and/or the dimples 76 can be located in other locations. Preferably, there is at least one dimple 76a located near the top or upper region of the container 18a for forming a venting hole and at least one dimple 76b located near the bottom or lower region of the container for forming a dispensing hole. Additionally, there is preferably at least one dimple 76c located at the end or rearward region of the container 18a for forming a dispensing hole to be utilized when the patient is laying down or a venting hole when the patient is bent or laying forward. Furthermore, there is preferably at least one dimple 76d located at the other end or forward region of the container for forming a dispensing hole to be utilized when the patient is bent or laying forward and/or as a venting hole when the patient is laying down. It is noted that having dimples 76 in both the forward and rearward regions also enables the container 18a to be interchangeably utilized in either side of the patient's mouth. There is preferably a plurality of dimples 76 in each region so that the flow rate can be varied by piercing a different quantity of dimples 76.

To form venting and dispensing holes, the patient merely pierces the thinned container wall at selected dimples 76 using a piercing tool. The diameter of the holes can also be varied such as, for example, by using a piercing tool having an increasing diameter so that the diameter of the holes are increased by increasing the depth of penetration of the tool.

The size, quantity and location, of the holes are selected and formed from the various dimples 76 to obtain a desired flow rate over a desired extended delivery period for particular conditions of the patient. Therefore, the container 18a can have a larger or smaller quantity of dispensing and/or venting holes, the holes can be located at various locations, and/or the holes can have various diameters depending on the active agent, the desired flow rate, the desired extended delivery period, and the orientation of the container 18a in use.

The container 18a also has a separate filling hole 78 which is located at generally the center of the outer side 26. The filling hole 78, however, can be located at any suitable location such, for example, the inner side 24. The filling hole 78 has a diameter, typically a diameter of at least $1/16$ inch, suitable for filling the container 18 with the active agent.

The fill hole is covered with a removable tape 32 having a face stock for closing the hole and an adhesive for securing the face stock to the container 18a. The removable tape 32 is also preferably in compliance with FDA regulations for direct food contact. A removable tape which provides adequate results is available from Visual Marking Systems, Inc., Twinsburg, Ohio and has a semigloss paper face stock and a TDF 900 general purpose latex adhesive. The removable tape 32 is placed over the filling hole 78 to retain the active agent in the container 18a once the container 18a has been filled. Thereafter, the tape 32 is not required to be removed unless the container 18a is to be refilled. It is noted that the filling hole 78 can be closed with other suitable closures or plugs.

Figure 21:
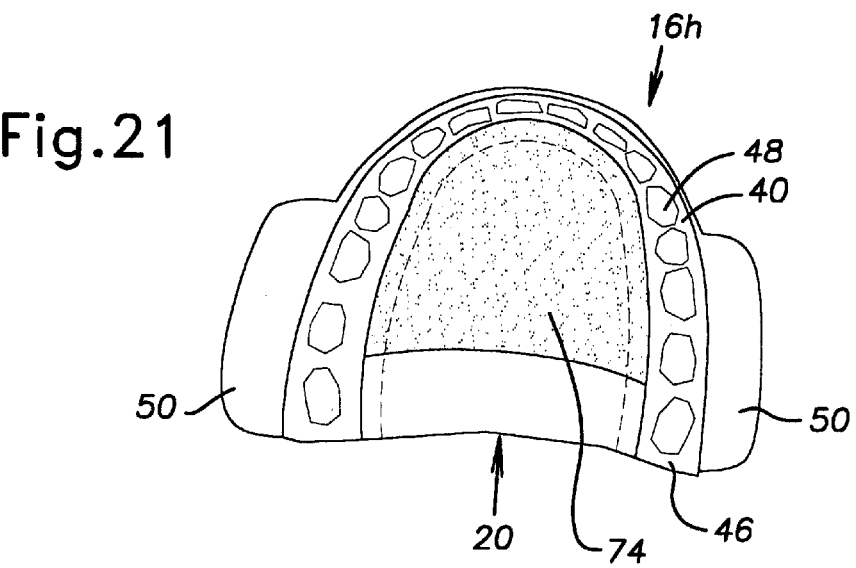
FIG. 21 is a plan view of medical reservoir system according to a ninth embodiment of the present invention.
Figure 22:
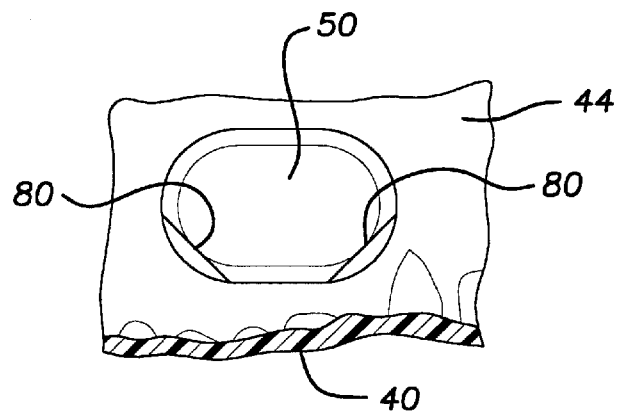
FIG. 22 is a cross-sectional view taken along line 22—22 of FIG. 21.
Figure 23:
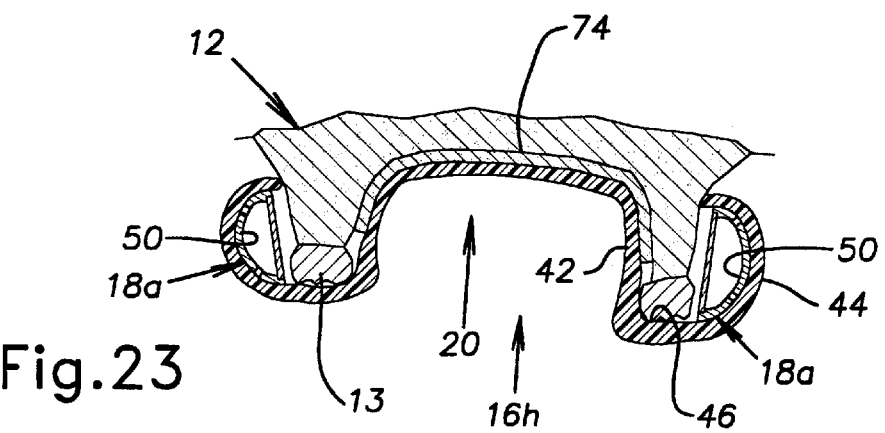
FIG. 23 is a diagrammatic view in cross-section of the medical reservoir system of FIG. 21 secured to a patient's maxilla.

FIGS. 21–23 illustrate a medical reservoir system 16h according to a ninth embodiment of the present invention. The medical reservoir system 16h is similar to the systems discussed above and like reference numbers are used for like structure. The medical reservoir system 16h illustrates that a relatively large quantity of the foraminous medium 74 can be used to hold and dispense a relatively large quantity of the active agent so that the container 18a can be of a reduced size.

The foraminous medium 74 is located on the upper side of the palatal flange 42 and covers substantially the entire palatal flange 42 bridging from one leg of the U-shaped channel 46 to the other. Located in this manner, the foraminous medium 74 is located adjacent and in contact with the patient's palate and above the patient's tooth/gum line. The foraminous medium 74 is sized to hold a relatively large quantity of the active agent. The foraminous medium 74 preferably holds about 10% to about 30%, and more preferably about 20%, of the total volume of active agent held by the reservoir system 16h. A desired total volume of active agent can be obtained, therefore, with containers 18a sized to hold a smaller volume of active agent. It is noted that the reduced size of the containers 18a results in increased patient comfort.

A medical reservoir system 16h for dispensing artificial saliva which is believed to obtain particularly good results has containers 18a sized to hold about 1.6 cm$^3$ of artificial saliva each. Such containers 18a have a length L of about 26 mm, a height H of 19 mm, and a width W of about 9 mm. The foraminous medium 74 is sized to hold about 0.8 cm$^3$ of artificial saliva, or about 20% of the total volume of active agent.

It should be appreciated that the illustrated location of the foraminous medium 74 holds a relatively large volume of the active agent and also directly locates the active agent in an advantageous location within the oral cavity. The foraminous medium 74 provides a supply of the active agent at the palate above the containers 18a such that, when the patient is standing, the active agent downwardly flows over surfaces in the oral cavity located above the containers 18a, which are not directly in the gravity fed flow of active agent from the containers 18a.

As best shown in FIG. 22, the openings of the chambers 50 of the appliance 20 are preferably provided with lugs 80. The lugs 80 are sized and shaped to retain or secure the container 18a in the chamber 18 yet allow the container 18a to be removed from the chamber 50 when desired. In the illustrated embodiment, there are two lugs, one located at a front/bottom portion of the opening and one located at a rear/bottom portion. It is noted that lugs 80 can have other suitable shapes and/or locations.

Although particular embodiments of the invention have been described in detail, it will be understood that the invention is not limited correspondingly in scope. For example, the illustrated embodiments of the present invention each disclose reservoir systems for use in human oral cavities but reservoir systems for use in animal oral cavities are within the scope of the present invention. Therefore, the present invention includes all changes and modifications coming within the spirit and terms of the claims appended hereto.

What is claimed is:

1. A reservoir system for delivering an active agent into an oral cavity of a patient over an extended delivery period, said reservoir system comprising:

at least one container for holding the active agent;

a foraminous medium for holding and dispensing the active agent;

a molded plastic appliance for overlying teeth of the patient and for securing said at least one container within the oral cavity at a desired location, wherein said appliance forms a chamber, at least one container being located within said chamber, and a palatal flange with said foraminous medium secured to said palatal flange.

2. The reservoir system according to claim 1, wherein said foraminous medium is sized to hold about 20% of a total volume of the active agent.

3. The reservoir system according to claim 1, wherein said appliance has a main wall, said palatal flange extending from the main wall, and a buccal flange extending from the main wall, wherein said main wall, said palatal flange, and said buccal flange cooperate to form a generally U-shaped channel, said palatal flange and said foraminous medium extending from one leg of said channel to the other leg of said channel.

4. The reservoir system according to claim 1, wherein said appliance is molded from a flexible plastic and said foraminous medium is imbedded in the plastic.

5. A container for delivering an active agent into an oral cavity over an extended delivery period, said container comprising a body having a size and shape suitable for comfortably residing in the oral cavity for the extended delivery period, said body having wall portions forming a hollow interior space for containing the active agent and forming its exterior surface, and a plurality of dimples being formed at spaced locations on the exterior surface of the body, the dimples being relatively small in comparison to the area of the exterior surface, said dimples providing localized zones in the wall portions of the body where the wall thickness of the body is relatively thin in comparison to the wall thickness of major parts of the body, the dimples by virtue of their exterior locations on the exterior surface of the body indicating where the wall portions of the body are thin and assisting puncture of the wall portions for venting and dispensing purposes by receiving and guiding a puncturing tool used to pierce the wall of the body.

6. The container according to claim 5, wherein said body has a length of about 26 mm, a height of about 19 mm, and width of about 9 mm.

7. The container according to claim 5, wherein said body is formed of a rigid plastic impermeable to fluids.

8. The container according to claim 5, wherein said body is cabochon shaped having a generally flat inner side and a generally convex outer side such that said container is unsymmetrical.

9. The container according to claim 8, wherein said dimples are spaced about a periphery of said inner side.

10. The container according to claim 5, wherein said dimples are spaced about a periphery of said body.

11. The container according to claim 5, wherein at least one of said dimples is located at a top portion of said body and at least one of said dimples is located at a bottom portion of said body.

12. The container according to claim 11, wherein at least one of said dimples is located at an end portion of said body and at least one of said dimples is located at an opposite end portion of said body.

13. A reservoir system for delivering an active agent into an oral cavity of a patient over an extended delivery period, said reservoir system comprising:

a foraminous medium for holding and dispensing the active agent; and a molded plastic appliance for overlaying teeth of the patient and for holding said foraminous medium at a desired treatment location within the oral cavity, said appliance having a main wall, a palatal flange extending from the main wall, and a buccal flange extending from the main wall, wherein said main wall, said palatal flange, and said buccal flange cooperate to form a generally U-shaped channel with two legs, wherein said foraminous medium is secured to said palatal flange and said palatal flange and said foraminous medium extend from one leg of said channel to the other leg of said channel.

14. The reservoir system according to claim 13, wherein said appliance is molded from a flexible plastic and said foraminous medium is imbedded in the plastic.

* * * * *